United States Patent
Dubois

(10) Patent No.: US 8,377,661 B2
(45) Date of Patent: Feb. 19, 2013

(54) METHOD FOR SYNTHESISING OMEGA-AMINO-ALKANOIC ACIDS OR THE ESTERS THEREOF FROM NATURAL FATTY ACIDS

(75) Inventor: Jean-Luc Dubois, Millery (FR)

(73) Assignee: Arkema France, Colombes (FR)

( * ) Notice: Subject to any disclaimer, the term of this patent is extended or adjusted under 35 U.S.C. 154(b) by 292 days.

(21) Appl. No.: 13/001,674

(22) PCT Filed: Jul. 9, 2009

(86) PCT No.: PCT/FR2009/051369
§ 371 (c)(1),
(2), (4) Date: Dec. 28, 2010

(87) PCT Pub. No.: WO2010/004219
PCT Pub. Date: Jan. 14, 2010

(65) Prior Publication Data
US 2011/0104764 A1 May 5, 2011

(30) Foreign Application Priority Data
Jul. 10, 2008 (FR) ...................... 08 54709

(51) Int. Cl.
*C12P 13/00* (2006.01)
*C07C 229/00* (2006.01)
*C07C 205/00* (2006.01)
(52) U.S. Cl. .......................... 435/128; 560/155; 562/553
(58) Field of Classification Search .................. 435/128; 560/155; 562/553
See application file for complete search history.

(56) References Cited

U.S. PATENT DOCUMENTS

| | | | |
|---|---|---|---|
| 3,823,070 | A | 7/1974 | Minato et al. |
| 3,912,586 | A | 10/1975 | Kaneyuki et al. |
| 4,474,882 | A | 10/1984 | Kunishige et al. |
| 5,254,466 | A | 10/1993 | Picataggio et al. |
| 6,569,670 | B2 | 5/2003 | Anderson et al. |
| 6,660,505 | B2 | 12/2003 | Staley |
| 7,576,227 | B2 | 8/2009 | Lysenko et al. |

FOREIGN PATENT DOCUMENTS

| | | |
|---|---|---|
| GB | 743491 | 1/1956 |
| GB | 2043052 | 10/1980 |

OTHER PUBLICATIONS

Aharoni, S., "n-Nylons: Their Synthesis, Structure, and Properties" John Wiley & Sons, (1997), pp. 381-389.

Pryde, E., et al., "Aldehydic Materials by the Ozonization of Vegetable Oils", The Journal of the American Oil Chemists Society, vol. 39 (1962), pp. 496-500.
Mol, J., "Catalytic metathesis of unsaturated fatty acid esters and oils*", Topics in Catalysis, vol. 27, (2004), pp. 97-104.
Schaverien, C., et al., "A Well-Characterized, Highly Active, Lewis Acid Free Olefin Metathesis Catalyst", J. Am. Chem. Soc., 108, (1986), pp. 2771-2773.
Couturier, J.-L., et al., "A Cyclometalated Aryloxy(chloro)neopentylidenetungsten Complex: A Highly Active and Stereoselective Catalyst for the Metathesis of cis- and trans-2-Pentene, Norbornene, 1-Methylnorbornene, and Ethyl Oleate**", Angew. Chem. Int. Ed. Engl., 31, No. 5, (1992), pp. 628-631.
Schwab, P., et al., "A Series of Well-Defined Metathesis Catalysts Synthesis of [RuCl2(=CHR)(PR3)2] and Its Reactions**", Angew. Chem. Int. Ed. Engl., 34, No. 18, (1995) pp. 2039-2041.
Throckmorton, P., "Pilot Run, Plant Design and Cost Analysis for Reductive Ozonolysis of Methyl Soyate", The Journal of the American Oil Chemists Society, vol. 49, No. 11, (1999), pp. 643-648.
Perkins, R., et al., "Nylon-9 from Unsaturated Fatty Derivatives: Preparation and Characterization", The Journal of the American Oil Chemists Society, vol. 52, (1975), pp. 473-477.
Ullmann's Encyclopedia of Industrial Chemistry, 5th Edition, vol. A8, (987), pp. 523-539.
Scholl, M., et al., "Synthesis and Activity of a New Generation of Ruthenium-Based Olefin Metathesis Catalysts Coordinatedwith 1.3-Dimesityl-4. 5-dihydroimidazol-2-ylidene Ligands", Organic Letters, vol. 1, (1999), pp. 953-956.
Eschenfeldt, W., et al., "Transformation of Fatty Acids Catalyzed by Cytochrome P450 Monooxygenase Enzymes of Candida tropicalis", Appiled and Environmental Microbiology, vol. 69, (2003), pp. 5992-5999.
Drawert, F., et al., "Bildung von 9-Oxo-nonansauremethylester und 12-Oxo-dodecensauremethylester aus Linol-und Linolsauremethylester und von 9-Oxo-nonansaure aus Sonnenblumenol durch Bestrahlung mit 6 Mrad*", Chem. Mikrobiol. Technol. Lebensm, (1972), pp. 158-159.
Zhang, G., et al., "Study on Oxidations of Benzilic Ethers, Oximes and 1,2-Diols by Ammonium Chlorochromate", Chinese Chemical Letters, vol. 5, (1994), pp. 105-108.
Schwartz, C., et al. "'Reductive ozonolysis' via a new fragmentation of carbonyl oxides", Tetrahedron, (2006), pp. 10747-10752.
Miller, W., et al., "Nylon-9 Via 9-Aminononanoic Acid from Soybean Oil", Ind.Eng. Chem. Prod. Res. Develop., vol. 10, (1971), pp. 442-447.
Kohlhase, W., et al., "9-Aminononanamide and Nylon-9 From Azelaaldehydic Derivatives of Soybean Oil", Journal of the American Oil Chemists Society, vol. 47, (1970), pp. 183-188.
Mol, J., "Application of olefin metathesis in oleochemistry: an example of green chemistry", Green Chemistry, vol. 4, (2002), pp. 5-13.

*Primary Examiner* — Herbert J Lilling
(74) *Attorney, Agent, or Firm* — Smith, Gambrell & Russell, LLP

(57) ABSTRACT

The invention relates to a method for synthesizing ω-amino-alkanoic acids or the esters thereof from mono-unsaturated natural fatty acids comprising at least one step of forming the unsaturated diacid corresponding to the original fatty acid.

7 Claims, No Drawings

METHOD FOR SYNTHESISING OMEGA-AMINO-ALKANOIC ACIDS OR THE ESTERS THEREOF FROM NATURAL FATTY ACIDS

FIELD OF THE INVENTION

The present invention relates to a novel process for synthesizing supramolecular materials, and also to the materials obtained and to the uses thereof.

BACKGROUND OF THE INVENTION

The invention is directed toward a process for synthesizing ω-aminoalkanoic acids, or esters thereof, from monounsaturated natural fatty acids, comprising at least one step of forming the unsaturated diacid corresponding to the original fatty acid.

The polyamide industry uses an entire range of monomers consisting of long-chain ω-amino acids, usually called Nylon, characterized by the length of methylene chain $(-CH_2)_n$ separating the amide functions $-CO-NH_2-$. The following are thus known: Nylon-6, Nylon 6-6, Nylon 6-10, Nylon 7, Nylon 8, Nylon 9, Nylon 11, Nylon 13, etc. These Nylon polymers are often, in the interests of simplification, referred to as PA (for PolyAmide), combining therewith the number of carbon atoms of the molecule: Nylon 8=PA 8, for example.

These monomers are, for example, produced by chemical synthesis using, in particular, as starting material, $C_2$ to $C_4$ olefins, cycloalkanes or benzene, but also castor oil (Nylon 11), erucic or lesquerolic oil (Nylon 13), etc.

The current change in environmental matters is resulting, in the energy and chemistry fields, in preference being given to the exploitation of natural starting materials originating from a renewable source. For this reason, certain studies have been resumed in order to develop, from the industrial point of view, methods using fatty acids/esters as starting material for the production of these monomers.

This type of approach has only a few industrial examples. One of the rare examples of an industrial process using a fatty acid as starting material is that of the production, from ricinoleic acid extracted from castor oil, of 11-aminoundecanoic acid, which is the basis for the synthesis of Rilsan 11°. This process is described in the book "Les Procédés de Pétrochimie" [Petrochemistry processes] by A. Chauvel et al., published by Editions TECHNIP (1986). 11-Aminoundecanoic acid is obtained in several steps. The first consists of a methanolysis of castor oil in a basic medium, producing methyl ricinoleate, which is then subjected to pyrolysis so as to obtain, on the one hand, heptanaldehyde and, on the other hand, methyl undecylenate. The latter is converted into acid form by hydrolysis. The acid formed is then subjected to hydrobromination to give ω-bromo acid, which is converted via amination into 11-aminoundecanoic acid.

Much work has been carried out in order to synthesize 9-aminononanoic acid or 9-aminoazelaic acid, corresponding to Nylon 9, from oleic acid of natural origin.

Mention may be made of the book "n-Nylons, Their Synthesis, Structure and Properties"-1977, Ed. J. Wiley and Sons, chapter 2.9 of which (pages 381 to 389) is devoted to 9-Nylon. This article summarizes the preparations and studies carried out on the subject. Mention is made therein, on page 384, of a process, apparently industrial, developed in Japan using oleic acid which comes from soya oil as starting material. The corresponding description makes reference to the book by A. Ravve "Organic Chemistry of Macromolecules" (1967), Marcel Dekker, Inc., section 15 of which is devoted to polyamides and which mentions, on page 279, the existence of such a process.

To be complete regarding the prior art on the subject, mention should be made of the numerous articles published by E. H. Pryde et al. between 1962 and 1975 in—Journal of the American Oil Chemists' Society—"Aldehydic Materials by the Ozonization of Vegetable Oils" Vol. 39 pages 496-500; "Pilot Run, Plant Design and Cost Analysis for Reductive Ozonolysis of Methyl Soyate" Vol. 49 pages 643-648 and "Nylon-9 from Unsaturated Fatty Derivatives: Preparation and Characterization" Vol. 52 pages 473-477. These articles are essentially devoted to the reaction for reductive ozonolysis of the unsaturated fatty acid. Specifically, since it is well known, as is described in the Ullmann encyclopedia, 5th edition, Vol. A8, pages 523 to 539, that the synthesis of diacids can be obtained by oxidative degradation of unsaturated fatty acids, it is essential that the oxidation reaction be carried out under milder conditions in order to block the reaction and obtain the aldehyde-acid CHO—R—COOH, which is a precursor of the ω-amino acid.

DETAILED DESCRIPTION OF THE INVENTION

The invention aims to propose a novel route for the synthesis of long-chain ω-amino acids starting from natural fatty acids originating from a renewable source.

The solution proposed consists in working by starting from starting materials consisting of natural long-chain monounsaturated fatty acids. The term "natural fatty acid" is intended to mean an acid which is derived from plant or animal environments, including algae, more generally from the plant kingdom, and which is therefore renewable. This acid will contain at least 10, and preferably at least 14, carbon atoms per molecule and an olefinic unsaturation.

By way of examples of such acids, mention may be made of obtusilic (4-decenoic) acid, caproleic (9-decenoic) acid, lauroleic (5-dodecenoic) acid, linderic (4-dodecenoic) acid, myristoleic (cis-9-tetradecenoic) acid, physeteric (cis-5-tetradecenoic) acid, tsuzuic (cis-4-tetradecenoic) acid, palmitoleic (cis-9-hexadecenoic) acid, the $C_{is}$ acids oleic (cis-9-octadecenoic) acid, elaidic (trans-9-octadecenoic) acid, petroselenic (cis-6-octadecenoic) acid and vaccenic (cis-11-octadecenoic) acid, the $C_{20}$ acids gadoleic (cis-9-eicosenoic) acid and gondoic (cis-11-eicosenoic) acid, the $C_{22}$ acids cetoleic (cis-11-docosenoic) acid and erucic (cis-13-docosenoic) acid, and the $C_{24}$ acid nervonic (cis-15-tetracosenoic) acid.

The list of natural monounsaturated fatty acids with their main characteristics is given in table 1 below.

TABLE 1

| Name according to the international standard | Common name | Abbreviated designation | Molecular mass | Melting point (° C.) |
|---|---|---|---|---|
| cis-4-decenoic | obtusilic | 10:1 (n-6) | 170.3 | |
| cis-9-decenoic | caproleic | 10:1 (n-1) | 170.3 | |
| cis-5-lauroleic | lauroleic | 12:1 (n-7) | 198.4 | |
| cis-4-dodecenoic | linderic | 12:1 (n-8) | 198.4 | |

TABLE 1-continued

| Name according to the international standard | Common name | Abbreviated designation | Molecular mass | Melting point (° C.) |
|---|---|---|---|---|
| cis-9-tetradecenoic | myristoleic | 14:1 (n-5) | 226.4 | |
| cis-5-tetradecenoic | physeteric | 14:1 (n-9) | 226.4 | |
| cis-4-tetradecenoic | tsuzuic | 14:1 (n-10) | 226.4 | |
| cis-9-hexadecenoic | palmitoleic | 16:1 (n-7) | 254.4 | 0.5 |
| cis-6-octadecenoic | petroselinic | 18:1 (n-12) | 282.4 | 30 |
| cis-9-octadecenoic | oleic | 18:1 (n-9) | 282.4 | 16.2 |
| trans-9-octadecenoic | elaidic | tr18:1 (n-9) | 282.4 | 43.7 |
| cis-11-octadecenoic | vaccenic | 18:1 (n-7) | 282.4 | 39 |
| cis-9-eicosenoic | gadoleic | 20:1 (n-11) | 310.5 | 25 |
| cis-11-eicosenoic | gondoic | 20:1 (n-9) | 310.5 | — |
| cis-11-docosenoic | cetoleic | 22:1 (n-11) | 338.6 | |
| cis-13-docosenoic | erucic | 22:1 (n-9) | 338.6 | 33.4 |
| cis-15-tetracosenoic | nervonic | 24:1 (n-9) | 336.6 | 39 |

The subject of the invention is a process for synthesizing ω-aminoalkanoic acids, or esters thereof, from monounsaturated natural fatty acids, characterized in that, in a first step, the monounsaturated natural fatty acid having the following general formula R—$(CH_2)_m$—CH=CH—$(CH_2)_p$—COOH, in which R is either H or $CH_3$, m is an index having a value of between 0 and 11 and p is an index having a value of between 2 and 13, is converted into an unsaturated α-ω-diacid or diester either by a homometathesis reaction or by fermentation, and then, in a second step, the unsaturated α-ω-diacid or diester formed is subjected to an oxidative cleavage reaction so as to form a single α-ω-aldehyde-acid or ester or two different α-ω-aldehyde-acids or esters (depending on whether or not the unsaturated α-ω-diacid or diester is symmetrical) of general formula CHO—$(CH_2)_n$—COOH, in which n is equal to m and/or p, and then, finally, the resulting product is converted, by reductive amination, into an ω-amino acid of formula $NH_2$—$(CH_2)_{n+1}$—COOH.

When the first step is carried out by homometathesis, the reaction is the following:

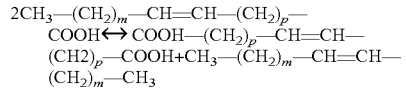

and the diacid is separated from the olefin by extraction, crystallization, separation by settling out or, optionally, vacuum distillation, before being subjected to the second step.

When the first step is carried out by fermentation, the acid is converted into a diacid: COOH—$(CH_2)_m$—CH=CH—$(CH_2)_p$—COOH and extracted from the fermentation medium before being subjected to the second step. While, in the case of fermentation, the diacid is indeed obtained, it is, on the other hand possible to obtain the diacid or the diester via the homometathesis route, according to the starting product.

The metathesis reactions that can be used in the first step of the process have been known for a long time, even though their industrial applications are relatively limited. In relation to their use in the conversion of fatty acids (esters), reference may be made to the article by J. C. Mol "Catalytic metathesis of unsaturated fatty acid esters and oil" published in Topics in Catalysis Vol. 27, Nos. 1-4, February 2004 (Plenum Publishing Corporation).

Catalysis of the metathesis reaction has been the subject of a very large number of studies and the development of sophisticated catalytic systems. Mention may be made, for example, of the tungsten complexes developed by Schrock et al. (J. Am. Chem. Soc. 108 (1986) 2771) or Basset et al. (Angew. Chem., Ed. Engl. 31 (1992) 628). More recently "Grubbs" catalysts have emerged (Grubbs et al. Angew. Chem., Ed. Engl. 34 (1995) 2039 and Organic Lett. 1 (1999) 953), which are ruthenium-benzylidene complexes. This is homogeneous catalysis. Heterogeneous catalysts based on metals such as rhenium, molybdenum and tungsten, deposited on alumina or silica, have also been developed. Finally, studies have been carried out in order to prepare immobilized catalysts, i.e. catalysts of which the active ingredient is that of the homogeneous catalyst, in particular ruthenium-carbene complexes, but which is immobilized on an inactive support. The objective of these studies is to gain a better understanding of the selectivity of the reaction with respect to the parasitic reactions between the reactants brought together. They relate not only to the structure of the catalysts, but also to the effect of the reaction medium and the additives that may be introduced.

In the process of the invention, any active and selective metathesis catalyst may be used. Ruthenium-based catalysts will, however, preferably be used.

The metathesis reaction of the first step is carried out at a temperature of between 20 and 100° C. and at a pressure of between 1 and 5 bar.

When the first step is carried out by fermentation, use is made of a microorganism, such as a bacterium, a fungus or a yeast, which makes possible the oxidation of the fatty acid or ester of the feedstock. Use will preferably be made of microorganisms containing enzymes of Oxygenase type which are capable of oxidizing the feedstock, forming a trivalent function of acid —COOH or ester —COOR type.

This fermentation may, for example, be carried out in the presence of a strain of *Candida tropicalis* containing cytochrome P450 monooxygenase enzymes, such as those described in the publication by W. H. Eschenfeldt et al., "Transformation of fatty Acids Catalyzed by Cytochrome P450 Monooxygenase Enzymes of *Candida tropicalis*" published in Applied and Environmental Microbiology, October 2003, pp. 5992-5999 and patents FR 2,445,374, U.S. Pat. Nos. 4,474,882, 3,823,070, 3,912,586, 6,660,505, 6,569,670 and 5,254,466.

The second step of the process consists of an oxidative cleavage of the double bond of the diacid.

The reaction for oxidative cleavage of the double bond, which results in the formation of aldehyde functions on the two carbons of the double bond, is also known per se. It can be carried out by means of a strong oxidizing agent such as $KMnO_4$ in concentrated form and with heat, as is described in "Organic Chemistry" by L. G. Wade Jr., 5th Edition, Chapter 8, Reactions of Alkenes. The oxidative cleavage may be carried out with aqueous hydrogen peroxide as described in patent GB 743491. The article by F. Drawert et al., in Chem. Mikrobiol. Technol. Lebensm. 1, 158-159 (1972), describes an alternative route by irradiation of sunflower oil. Furthermore, the article by G. S. Zhang et al., in Chinese Chemical Letters, Vol. 5, No. 2, pp. 105-108 from 1994, indicates that it is possible to carry out the oxidative cleavage starting from the diol corresponding to oleic acid (see Entry 29 in the table). This oxidative cleavage is carried out using ammonium chlorochromate as oxidizing agent. The dial is, for its part, obtained by epoxidation of oleic acid followed by hydrolysis of the epoxy bridge. It can be carried out by means of other oxidizing agents, such as aqueous hydrogen peroxide, and more particularly ozone.

However, it is necessary to avoid the oxidative reaction being complete, since, as was indicated above, the oxidation of an unsaturated acid is the well known synthesis route for the production of diacids. Operating conditions should therefore be envisioned such that the reaction stops at the aldehyde function. This is why, in the studies described in the prior art, the focus was on an oxidation reaction coupled with a reduction, often hydrogenation, of the products of the oxidation, very generally obtained by ozonolysis. The oxidation conditions should therefore be milder, in order to thus have better control of the process, by working in the presence of hydrogen combined with a catalyst and/or of a mild reducing agent. This is the reaction which is known as reductive ozonolysis.

The ozonolysis reaction has been the subject of considerable studies which have made it possible to reveal a "Criegee" reaction mechanism (cf. Article "Aldehydic Materials by the Ozonization of Vegetable Oils" Vol. 39 pages 496-500, mentioned above) marked by the formation of an ozonide.

The first phase of the reductive ozonolysis can be carried out in various solvent media. If it is carried out in the aqueous phase, the unsaturated fatty acid is present in the form of a water-in-oil emulsion. It can be carried out in an alcohol-type methanol, ethanol, propanol, butanol, methoxyethanol, cyclohexanol or benzyl alcohol solvent; when the ozonolysis is carried out on the fatty ester, it will be advantageous to use the alcohol R—OH corresponding to the fatty ester. The use of DMSO as solvent medium has also been proposed by Chris Schwartz, Joseph Raible, Kyle Mott, and Patrick H. Dussault, Tetrahedron 62 (2006), pp. 10747-10752. It is common to combine, with the alcohol solvent medium, an organic acid, generally acetic acid, which will generally be present in the form of an equimolar mixture with the alcohol.

The second phase of the reductive ozonolysis will consist of a reduction of the ozonide which can be carried out with zinc in acetic acid, a hydrogenation in the presence of a hydrogenation catalyst (Pd, for example) or using a reducing agent such as, for example, dimethyl sulfide (DMS).

The preferred variant embodiment of this step is reductive ozonolysis which may be carried out in the presence of zinc metal, in powder form, or else preferably in the presence of dimethyl sulfide (DMS: $CH_3$—S—$CH_3$); this is because this DMS will be converted, during the reductive ozonolysis, to DMSO which is a solvent widely used by the industry.

Finally, the reductive amination of the aldehyde function to give a primary amine is well known to those skilled in the art. The reductive amination of 9-oxononanoic acid obtained so as to form 9-aminononanoic acid can be carried out according to many catalytic or enzymatic methods, and for example according to the method described in patent application U.S. Pat. No. 5,973,208.

The reaction mechanisms of the process, in its two versions, can be summarized as follows:

1st step: homometathesis: formation of the fatty diacid

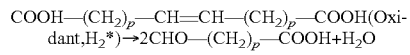

optionally followed by esterification after olefin elimination.

2nd step: after olefin elimination: oxidative cleavage (reductive ozonolysis)

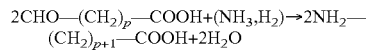

$H_2$* symbolizes, in reaction 3, the coupling of an oxidation followed by a reduction.

3rd step: Reductive amination

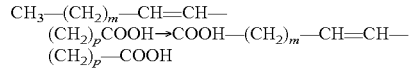

and, in the case of fermentation,

1st step: fermentation: formation of the fatty diacid

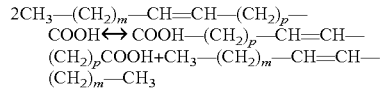

optionally followed by an esterification

2nd step: after extraction of the diacid: oxidative cleavage (reductive ozonolysis)

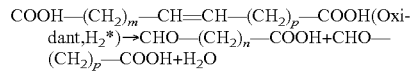

3rd step: Reductive amination

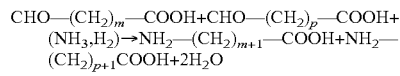

When the first step of fermentation or of homometathesis/olefin elimination is followed by an esterification and then oxidative cleavage and reductive amination steps, an ester amine is obtained which can be distilled and polymerized directly (production of methanol) or hydrolyzed to an amino acid and then polymerized.

Thus, by applying these reaction mechanisms to the various fatty acids mentioned in Table 1, it is possible to produce the following products.

PA 9 via the caproleic acid homometathesis route.

Lauroleic acid results, via the homometathesis route, in PA 5, and via the fermentation route, in a mixture of PA 5 and PA 7 which do not exhibit any especially advantageous properties in the polymerization application.

Linderic acid results, via the homometathesis route, in PA 4 and, via the fermentation route, in a mixture of PA 4 and of PA 8 which is of little interest.

Myristoleic acid results, via the homometathesis route, in PA 9 and, via the fermentation route, in a mixture of PA 9 and PA 5.

Physiteric acid results, via the homometathesis route, in PA 5 and, via the fermentation route, in a mixture of PA 5 and of PA 9.

Tsuzuic acid results, via the homometathesis route, in PA 4 and, via the fermentation route, in a mixture of PA 4 and of PA 10.

Palmitoleic acid results, via the homometathesis route, in PA 9 and, via the fermentation route, in a mixture of PA 9 and of PA 7.

Petroselenic acid results, via the homometathesis route, in PA 6 and, via the fermentation route, in a mixture of PA 6 and of PA 12.

Oleic acids result, via both routes, in PA 9 with a double yield since it is the only product that can be obtained.

Vaccenic acid results, via the homometathesis route, in PA 11 and, via the fermentation route, in a mixture of PA 11 and of PA 7.

Gadoleic acid results, via the homometathesis route, in PA 9 and, via the fermentation route, in a mixture of PA 9 and of PA 11.

Gondoic acid results, via the homometathesis route, in PA 11 and, via the fermentation route, in a mixture of PA 9 and of PA 11.

Cetoleic acid results, via both routes, in PA 11 with a double yield.

Erucic acid results, via the homometathesis route, in PA 13 and, via the fermentation route, in a mixture of PA 13 and of PA 9.

Nervonic acid results, via the homometathesis route, in PA 15 and, via the fermentation route, in a mixture of PA 15 and of PA 9.

As can be seen, the process applied to certain natural fatty acids, the symmetrical unsaturated fatty acids (m=p), makes it possible to obtain performance levels and yields which are quite exceptional since, with just one molecule of fatty acid, 2 molecules of ω-amino acids are obtained. These are 9-aminononanoic acid (PA 9) derived from $C_{18}$ oleic acids and 11-aminoundecanoic acid (PA 11) derived from cetoleic acid, which constitute particularly advantageous polymerization monomers.

Naturally, the economic criterion, alongside the technical performance levels, plays a predominant role. Some of these acids are widely available, which gives them un undeniable advantage from the moment that they are capable of resulting in an industrializable monomer.

Among these acids, mention may be made of caproleic acid, myristoleic acid, palmitoleic acid and oleic acids which all lead to PA 9.

It can also be observed that the process carried out in the form of its fermentation variant makes it possible, with certain other natural fatty acids, to obtain mixtures of ω-amino acids which have similar and/or complementary structures, which mixtures are capable of being polymerized while resulting in performance levels similar to those obtained with pure monomers.

In this respect, mention may be made of:
myristoleic acid which results in a mixture of PA 5 and PA 9,
palmitoleic acid which results in a mixture of PA 7 and PA 9,
vaccenic acid which results in a mixture of PA 7 and PA 11,
gadoleic acid which results in a mixture of PA 9 and PA 11,
gondoleic acid which results in a mixture of PA 9 and PA 11, and
erucic acid which results in a mixture of PA 9 and PA 13.

The process of the invention is illustrated by the examples hereinafter.

EXAMPLE 1

Fermentation Route Applied to Oleic Acid

1st Step

In this example, a yeast containing at least one oxygenase enzyme will be used. The yeast will be cultured at pH=7, in a medium of deionized water containing sorbitol, trace elements, urea and oleic acid. The mixture will then be sterilized at 120° C. for 15 minutes. The culture medium will then be inoculated with a yeast strain. The culture will be maintained at 30° C. A solution of sodium hydroxide will be added continuously in order to maintain the medium at a pH of 7.0 to 7.5. After 48 hours of culture, the unsaturated diacid will be recovered by extraction with diethyl ether. After elimination of the solvent by evaporation, crystals will be recovered, said crystals having, after recristallization, a melting point of 69° C., i.e. equivalent to that described for 9-octadecenedioic acid.

2nd Step

The 9-octadecenedioic acid of the first step will be dissolved in pentane saturated with ozone and subjected to reductive ozonolysis. This example illustrates the oxidative cleavage of the $C_{18}$ diacid resulting from example 1, by reductive ozonolysis.

1 mg of the diester of oleic acid: 1,18-dimethyl 9-octadecenoate, is dissolved in 2 ml of pentane saturated with ozone and precooled to −70° C. The pentane is evaporated off under a nitrogen stream and 1 ml of DMS is added to the ozonide obtained. After 30 minutes, the excess DMS is evaporated off under a nitrogen stream. The product is dissolved in a small amount of ether and is analyzed.

The yield of methyl 9-oxononanoate ester is 82 mol %.

3rd Step

The compound resulting from the second step, of formula $CHO-(CH_2)_7-COOH$, 9-oxononanoic acid, will be subjected to reductive amination under the following conditions.

50 g of aldehyde ester, 50 ml of liquid ammonia, 125 ml of alcohol and 6 g of Raney nickel are run into a 500 ml stainless steel autoclave.

Hydrogen is introduced at a pressure of 100 to 150 atmospheres and the autoclave is heated at 100-110° C. for 4 hours. Upon cooling, the hydrogen and the ammonia are driven off, the content is siphoned off and the autoclave is rinsed with alcohol. The content of the autoclave and the washing alcohol are combined, filter-dried on a Büchner funnel and placed in a vacuum distillation apparatus in the presence of nitrogen. The alcohol and the ammonia are driven off with a water pump and then with a vane pump. The crude amino ester, which is colored, is placed in a dropping funnel with a view to it being distilled in the apparatus described.

The distilled amino ester (38 g) is slightly colored. The yield is 76 mol %.

The amino ester can optionally be directly polymerized to give polyamide-9, by heating under vacuum in order to recover the methanol produced.

It is also possible to polymerize the amino acid. For this, the amino ester is hydrolyzed. The methyl 9-aminononanoate obtained from 28 g of aldehyde ester is placed in a dropping funnel so as to drop into a 2 liter three-necked round-bottomed flask surmounted by a long distillation column and containing one liter of boiling water. The reflux is regulated so as to distil the methanol formed, which makes it possible to monitor the reaction; the hydrolysis lasts 4 to 5 hours for the methyl ester. When the reaction is complete, hot filtration is carried out and the water is evaporated off. A product is obtained which is difficult to dry in a desiccator. However, if the wet product is washed with acetone and dried in a desiccator, 20 g of colorless crude amino acid are recovered.

EXAMPLE 2

Homometathesis Route Applied to Oleic Acid

1st Step

This example illustrates the (optional) second step of homometathesis of oleic acid to give the diacid of formula $COOH-(CH_2)_7-CH=CH-(CH_2)_7-COOH$.

For this second step, the bispyridine ruthenium complex catalyst (8) described in the publication by Chen-Xi Bai et al., Tetrahedron Letters, 46 (2005) 7225-7228 is used. The reaction is carried out in toluene, at a temperature of 50° C. and for 12 hours at a pressure of 100 kPa, with the ethylene which is formed being extracted during the reaction. The yield of 9-octadecenedioic acid is 85 mol %.

This product will be subjected to the treatment of the second and third steps described above, and 11-aminoundecanoic acid will be obtained.

The invention claimed is:

1. A process for synthesizing ω-aminoalkanoic acids, or esters thereof, from monounsaturated natural fatty acids, comprising;
   converting a monounsaturated natural fatty acid having the formula R—$(CH_2)_m$—CH=CH—$(CH_2)_p$—COOH, in which R is either H or $CH_3$, m has a value of between 0 and 11 and p has a value of between 2 and 13, into an unsaturated α-ω-diacid or diester, either by a homometathesis reaction or by fermentation, then,
   subjecting the unsaturated α-ω-diacid or diester to an oxidative cleavage reaction so as to form a single α-ω-aldehyde-acid or ester or two different α-ω-aldehyde-acids or esters of the general formula CHO—$(CH_2)_n$—COOH, in which n is equal to m and/or p, and then,
   converting the resulting product, by reductive amination, into an ω-amino acid of formula $NH_2$—$(CH_2)_{n+1}$—COOH.

2. The process as claimed in claim 1, further comprising subjecting the α-ω-diacid or diester to ozonolysis in a solvent medium and reducing conditions prior to said oxidative cleavage reaction.

3. The process as claimed in claim 2, characterized in that the reducing conditions are provided by hydrogen combined with zinc metal.

4. The process as claimed in claim 2, characterized in that the reducing conditions are provided by dimethyl sulfide.

5. The process as claimed in claim 1, characterized in that the homometathesis reaction is carried out at a temperature of between 20 and 100° C. and at a pressure of between 1 and 5 bar, in the presence of ruthenium-based catalysts.

6. The process as claimed in claim 1, characterized in that the fermentation is carried out in the presence of microorganisms containing enzymes of oxygenase type which oxidize the monounsaturated natural fatty acid, forming a trivalent function of acid —COOH or ester —COOR type.

7. The process as claimed in claim 1, further comprising subjecting the unsaturated α-ω-diacid or diester to esterification prior to said oxidative cleavage reaction.

* * * * *